(12) United States Patent
Kelleher et al.

(10) Patent No.: US 6,310,092 B1
(45) Date of Patent: Oct. 30, 2001

(54) METHODS FOR PREVENTING AND TREATING AUTOIMMUNE AND INFLAMMATORY DISEASE USING THIOETHER FURAN NITRONE COMPOUNDS

(75) Inventors: Judith A. Kelleher, Fremont; Kirk R. Maples, San Jose; Yong-Kang Zhang, Santa Clara, all of CA (US)

(73) Assignee: Centaur Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/505,716

(22) Filed: Feb. 17, 2000

Related U.S. Application Data

(60) Continuation of application No. 09/408,126, filed on Sep. 29, 1999, now Pat. No. 6,127,408, which is a division of application No. 09/245,130, filed on Jan. 14, 1999, now Pat. No. 5,998,469.

(60) Provisional application No. 60/071,626, filed on Jan. 16, 1998.

(51) Int. Cl.[7] ................................................ A61K 31/34
(52) U.S. Cl. .............................................................. 514/471
(58) Field of Search ............................................... 514/471

Primary Examiner—Amelia Owens
(74) Attorney, Agent, or Firm—Burns, Doane, Swecker & Mathis, LLP

(57) ABSTRACT

Disclosed are methods for preventing the onset of autoimmune or inflammatory diseases in mammals using a pharmaceutical composition containing a pharmaceutically acceptable carrier and an effective amount of a thioether furan nitrone compound.

16 Claims, No Drawings

METHODS FOR PREVENTING AND TREATING AUTOIMMUNE AND INFLAMMATORY DISEASE USING THIOETHER FURAN NITRONE COMPOUNDS

CROSS-REFERENCE TO RELATED APPLICATIONS

This application is a continuation of U.S. Ser. No. 09/408,126, filed Sep. 29, 1999 and issued on Oct. 3, 2000 as U.S. Pat. No. 6,127,408; which application is a divisional of U.S. Ser. No. 09/245,130, filed Jan. 14, 1999 and issued on Dec. 7, 1999 as U.S. Pat. No. 5,998,469; which application claims the benefit of U.S. Provisional Application No. 60/071,626, filed Jan. 16, 1998, which application is incorporated herein by reference in its entirety.

BACKGROUND OF THE INVENTION

1. Field of the Invention

This invention relates to novel thioether furan nitrone compounds and their use as therapeutic agents and analytical reagents. More particularly, this invention concerns novel thioether furan nitrone compounds and their use as therapeutics for treating and/or preventing neurological, autoimmune and inflammatory conditions in mammals and as analytical reagents for detecting free radicals.

2. State of the Art

Alzheimer's disease is a neurodegenerative condition in which nerve cells in the brain are systematically destroyed resulting in progressive memory loss, mental confusion and ultimately death. The National Institute on Aging (NIA) has recently estimated that about 4 million people in the United States are currently afflicted with Alzheimer's disease. At present, there is no treatment that effectively prevents the disease or reverses its symptoms.

In recent years, significant progress has been made in understanding the pathogenesis of Alzheimer's disease. For example, it is now known that patients with Alzheimer's disease develop amyloid plaque deposits around and between the nerve cells of their brain. These plaque deposits are made up of fibrillar aggregates of a small peptide called amyloid β-peptide or Aβ. The plaque deposits initially form in the hippocampus and cortical regions of the brain (areas associated with memory and cognition) and then spread to other areas as the disease progresses. The deposition of fibrils and plaques is also followed by inflammation of the surrounding support cells, called glia, which may lead to further loss of neurons. The nerve cells in the brains of most Alzheimer's patients also develop tangles of a microtubule-associated protein, called tau, which are believed to be a response by the nerve cells to damage.

Progress in understanding the underlying mechanisms of Alzheimer's disease has led to the development of various in vitro and in vivo models to identify compounds effective for preventing and/or treating Alzheimer's disease and other neurodegenerative conditions. In one such in vitro model, compounds are evaluated for their ability to intervene in Aβ(1–40) or Aβ(1–42) beta-pleated sheet formation. Since the deposition of amyloid β-peptide is associated with the development of Alzheimer's disease, compounds which effectively disrupt the formation of Aβ(1–40) beta-pleated sheets are potentially useful for preventing and/or reversing Alzheimer's disease-related amyloid deposits.

In another in vitro model, compounds are evaluated for their ability to protect against Aβ(25–35)-induced neuronal cell loss in rat embryonic hippocampal neuronal/astrocyte cultures. As discussed above, patients with Alzheimer's disease suffer a progressive loss of neuronal cells. Accordingly, compounds which are effective in this in vitro test are potentially useful for reducing or preventing neuronal cell loss in patients afflicted with Alzheimer's disease or other neurodegenerative conditions.

A third in vitro Alzheimer's disease model is based on the observation that β-amyloid increases the release of cytokines, such as interleukin-1β (IL-1β), interleukin 6 (IL-6) and tumor necrosis factor-α (TNFα), in human monocyte cells induced with lipopolysaccharide (LPS). IL-1β, IL-6 and TNFα are proteins associated with inflammatory and immune responses. As previously mentioned, the deposition of fibrils in the brains of Alzheimer's patients is associated with inflammation of the surrounding support cells. See, S. D. Yan et al., *Proc. Natl. Acad. Sci. USA*, 94, 5296 (1997). Thus, compounds effective in this in vitro test are potentially useful for reducing and/or preventing the inflammation associated with Alzheimer's disease.

Additionally, elevated levels of IL-1β, IL-6, TNFα and other cytokines are associated with a wide variety of inflammatory and autoimmune conditions, including septic shock, rheumatoid arthritis, erythema nodosum leprosy, meningococcal meningitis, multiple sclerosis, systemic lupus and the like. See, L. Sekut et al., *Drug News Perspect.* 1196, 9, 261; and A. Waage et al., *J. Exp. Med.* 1989, 170, 1859–1867. Accordingly, compounds which inhibit the production of such cytokines are potentially useful for treating such inflammatory and autoimmune conditions.

Thus, in another in vitro model, compounds are evaluated for their ability to reduce cytokine-induced neuronal cell damage in rat embryonic cortical cell cultures. As discussed above, cytokines are associated with a wide variety of inflammatory and autoimmune conditions. Accordingly, compounds which are effective in this in vitro test are potentially useful for reducing or preventing inflammatory or autoimmune conditions.

It has now been discovered that certain novel thioether furan nitrone compounds effectively inhibit the formation of Aβ(1–42) beta-pleated sheets and/or inhibit the release of cytokines, such as IL-1β and/or reduce cytokine-induced neuronal cell damage. Accordingly, such compounds are useful for the prevention and/or treatment of neurodegenerative, autoimmune and inflammatory conditions in mammals.

The thioether furan nitrone compounds of this invention are also useful as analytical reagents for detecting free radicals. In this regard, the compounds of this invention function as "spin traps" by reacting with unstable free radicals to form relatively stable free radical spin adducts which are observable by electron spin resonance (ESR) spectroscopy. Accordingly, when used as spin traps, the compounds of this invention allow free radicals to be identified and studied using ESR and related techniques.

SUMMARY OF THE INVENTION

This invention provides novel thioether furan nitrone compounds which are useful as therapeutics for treating and/or preventing neurological, autoimmune and inflammatory conditions in mammals and as analytical reagents for detecting free radicals. In particular, the compounds of this invention are useful for preventing and/or treating Alzheimer's disease.

Accordingly, in one of its composition aspects, this invention is directed to compounds of formula I:

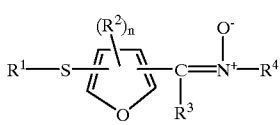

wherein $R^1$ is selected from the group consisting of alkyl, substituted alkyl, alkenyl, substituted alkenyl, alkynyl, aralkyl, aryl, cycloalkyl, cycloalkylalkyl, and cycloalkenyl;

each $R^2$ is independently selected from the group consisting of alkyl, substituted alkyl, alkenyl, substituted alkenyl, alkynyl, aralkyl, aryl, alkoxy, substituted alkoxy, cycloalkyl and halo;

$R^3$ is selected from the group consisting of hydrogen, alkyl, substituted alkyl, alkenyl, substituted alkenyl, alkynyl, aralkyl, aryl, cycloalkyl and cycloalkylalkyl;

$R^4$ is selected from the group consisting of alkyl, substituted alkyl, alkenyl, substituted alkenyl, alkynyl, aralkyl, aryl, cycloalkyl, cycloalkylalkyl and cycloalkenyl; and n is an integer ranging from 0 to 2; and optical isomers and racemates thereof, and pharmaceutically acceptable salts thereof.

In a preferred embodiment, $R^1$ is a substituted phenyl group having the formula:

wherein each $R^5$ is independently selected from the group consisting of alkyl, substituted alkyl, cycloalkyl, aralkyl, aryl, alkoxy, substituted alkoxy, aryloxy, aralkyloxy, cycloalkoxy, acyl, acylamino, aminocarbonyl, alkoxycarbonyl, carboxyl, cyano, halo, hydroxy, nitro, sulfonate, thioalkoxy, and —$NR^6R^7$, where $R^6$ and $R^7$ are each independently selected from hydrogen, alkyl, substituted alkyl or aryl; or two adjacent $R^5$ groups can be joined together to form an alkylene or alkylenedioxy group; and m is an integer from 1 to 5.

Preferably, $R^5$ is selected from the group consisting of alkyl, alkoxy, substituted alkoxy, acylamino, thioalkoxy. More preferably, $R^5$ is a methyl, methoxy, trifluoromethoxy, acetamido or thiomethoxy group. Preferably, when m is 1, the $R^5$ group is in the para position relative to the sulfur atom of the thio group.

Preferably, m is an integer from 1 to 3. More preferably, m is 1 or 2.

Particularly preferred $R^1$ groups include 2-methoxyphenyl, 4-methoxyphenyl, 4-trifluoromethoxyphenyl, 3,5-dimethylphenyl, 4-acetamidophenyl and 4-thiomethoxyphenyl.

Preferably, when present, $R^2$ is an alkyl group. More preferably, $R^2$ is a lower alkyl group.

$R^3$ is preferably selected from the group consisting of hydrogen and alkyl. More preferably, $R^3$ is hydrogen.

Preferably, $R^4$ is selected from the group consisting of alkyl, substituted alkyl, aralkyl, cycloalkyl and cycloalkylalkyl. More preferably, $R^4$ is alkyl, substituted alkyl, or cycloalkyl. Still more preferably, $R^4$ is alkyl or cycloalkyl.

Particularly preferred $R^4$ groups include n-propyl, isopropyl, 2,2-dimethyl-3-hydroxypropyl, n-butyl, isobutyl, sec-butyl, tert-butyl, n-pentyl, cyclopentyl, n-hexyl, cyclohexyl and 2,4,4-trimethylpent-2-yl (tert-octyl). Still more preferred $R^4$ groups include isopropyl, tert-butyl and cyclohexyl.

Preferably, n is 0 or 1. More preferably, n is 0.

In a preferred embodiment, this invention is directed to a compound of formula II:

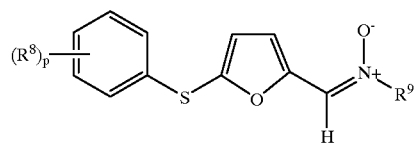

wherein each $R^8$ is independently selected from the group consisting of alkyl, alkoxy, acylamino, trifluoromethoxy and thioalkoxy;

$R^9$ is selected from the group consisting of alkyl and cycloalkyl; and p is an integer ranging from 1 to 3;

and optical isomers and racemates thereof, and pharmaceutically acceptable salts thereof.

Preferably, $R^8$ is a methyl, methoxy, trifluoromethoxy, acetamido or thiomethoxy group. Preferably, when p is 1, the $R^8$ group is in the para position relative to the sulfur atom of the thio group.

Preferably, p is 1 or 2.

Particularly preferred $R^9$ groups include n-propyl, isopropyl, n-butyl, isobutyl, sec-butyl, tert-butyl, n-pentyl, cyclopentyl, n-hexyl, cyclohexyl and 2,4,4-trimethylpent-2-yl (tert-octyl). Still more preferred $R^9$ groups include isopropyl, tert-butyl and cyclohexyl.

Particularly preferred thioether furan nitrone compounds include those having the formula shown in Table I.

TABLE I

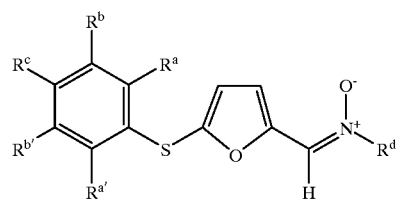

| Ex. | $R^a$ | $R^{a'}$ | $R^b$ | $R^{b'}$ | $R^c$ | $R^d$ |
|---|---|---|---|---|---|---|
| 1 | H | H | H | H | —$OCH_3$ | —$C(CH_3)_3$ |
| 2 | —$OCH_3$ | H | H | H | H | —$C(CH_3)_3$ |
| 3 | H | H | H | H | —$OCH_3$ | cyclohexyl |
| 4 | H | H | H | H | —$OCF_3$ | —$C(CH_3)_3$ |

TABLE I-continued

[Structure: A benzene ring with substituents R^a, R^a', R^b, R^b', R^c connected via S to a furan ring, which connects to CH=N^+(O^-)-R^d]

| Ex. | R^a | R^a' | R^b | R^b' | R^c | R^d |
|---|---|---|---|---|---|---|
| 5 | H | H | —CH₃ | —CH₃ | H | —C(CH₃)₃ |
| 6 | H | H | H | H | —NHC(O)CH₃ | —C(CH₃)₃ |
| 7 | H | H | H | H | —CH₂CH₃ | —C(CH₃)₃ |
| 8 | H | H | H | H | —SCH₃ | —C(CH₃)₃ |
| 9 | H | H | H | H | —OCH₃ | —CH(CH₃)₂ |
| 10 | H | H | H | H | —OCF₃ | cyclohexyl |
| 11 | H | H | H | H | —OCH₃ | —(CH₂)₃CH₃ |
| 12 | H | H | H | H | —OCH₃ | —(CH₂)₂CH₃ |
| 13 | H | H | H | H | —OCF₃ | —CH(CH₃)₂ |
| 14 | H | H | H | H | —OCF₃ | —(CH₂)₂CH₃ |
| 15 | H | H | H | H | —OCH₃ | —C(CH₃)₂CH₂C(CH₃)₃ |
| 16 | H | H | H | H | —OCF₃ | —C(CH₃)₂CH₂C(CH₃)₃ |
| 17 | H | H | H | H | —OCH₃ | cyclopentyl |
| 18 | H | H | H | H | —OCF₃ | cyclopentyl |

Accordingly, in another of its composition aspects, this invention is directed to each of the individual compounds:

α-[2-(4-methoxyphenylthio)-5-furyl]-N-tert-butylrntrone,

α-[2-(2-methoxyphenylthio)-5-furyl]-N-tert-butylnitrone,

α-[2-(4-methoxyphenylthio)-5-furyl]-N-cyclohexylnitrone,

α-[2-(4-trifluoromethoxyphenylthio)-5-furyl]-N-tert-butylnitrone,

α-[2-(3,5-dimethylphenylthio)-5-furyl]-N-tert-butylnitrone,

α-[2-(4-acetamidophenylthio)-5-furyl]-N-tert-butylnitrone,

α-[2-(4-ethylphenylthio)-5-furyl]-N-tert-butylnitrone,

α-[2-(4-thiomethoxyphenylthio)-5-furyl]-N-tert-butylnitrone,

α-[2-(4-methoxyphenylthio)-5-furyl]-N-isopropylnitrone,

α-[2-(4-trifluoromethoxyphenylthio)-5-furyl]-N-cyclohexylnitrone,

α-[2-(4-methoxyphenylthio)-5-furyl]-N-n-butylnitrone,

α-[2-(4-methoxyphenylthio)-5-furyl]-N-n-propylnitrone,

α-[2-(4-(trifluoromethoxyphenylthio)-5-furyl]-N-isopropylnitrone,

α-[2-(4-trifluoromethoxyphenylthio)-5-furyl]-N-n-propylnitrone,

α-[2-(4-methoxyphenylthio)-5-furyl]-N-2,4,4-trimethylpent-2-ylnitrone,

α-[2-(4-trifluoromethoxyphenylthio)-5-furyl]-N-2,4,4-trimethylpent-2-ylnitrone,

α-[2-(4-methoxyphenylthio)-5-furyl]-N-cyclopentylnitrone, and

α-[2-(4-trifluoromethoxyphenylthio)-5-furyl]-N-cyclopentylnitrone.

In another of its composition aspects, this invention is directed to pharmaceutical compositions comprising a pharmaceutically acceptable carrier and a pharmaceutically effective amount of a compound of formula I:

$$R^1-S-\text{[furan with }(R^2)_n\text{]}-C(R^3)=N^+(O^-)-R^4 \quad \text{I}$$

wherein R¹–R⁴ are as defined above.

In additional composition aspects, this invention is directed to pharmaceutical compositions comprising a pharmaceutically acceptable carrier and a pharmaceutically effective amount of a compound of formula II above.

As previously mentioned, the thioether furan nitrone compounds of this invention have been discovered to inhibit the formation of Aβ(1–42) beta-pleated sheets and/or to reduce β-amyloid-induced release of cytokines, such as IL-1β, in human monocyte cells and/or to reduce cytokine-induced neuronal cell damage. Compounds having such properties are useful for preventing and/or treating neurodegenerative, autoimmune and inflammatory conditions.

Accordingly, in one of its method aspects, this invention is directed to a method for treating a patient with a neurodegenerative disease which method comprises administering to said patient a pharmaceutical composition comprising a pharmaceutically acceptable carrier and an effective neurodegenerative disease-treating amount of a compound of formula I or formula II above.

In another of its method aspects, this invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a compound of formula I or formula II above.

In preferred embodiments of this invention, the neurodegenerative disease treated and/or prevented in the above methods is Alzheimer's disease, Parkinson's disease, HIV dementia and the like.

In still another of its method aspects, this invention is directed to a method for treating a patient with an autoimmune disease which method comprises administering to said patient a pharmaceutical composition comprising a pharmaceutically acceptable carrier and an effective autoimmune disease-treating amount of a compound of formula I or formula II above.

In yet another of its method aspects, this invention is directed to a method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a compound of formula I or formula II above.

In preferred embodiments of this invention, the autoimmune disease treated and/or prevented in the above methods is systemic lupus, multiple sclerosis and the like.

In still another of its method aspects, this invention is directed to a method for treating a patient with an inflammatory disease which method comprises administering to said patient a pharmaceutical composition comprising a pharmaceutically acceptable carrier and an effective inflammatory disease-treating amount of a compound of formula I or formula II above.

In yet another of its method aspects, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a compound of formula I or formula II above.

In preferred embodiments of this invention, the inflammatory disease treated and/or prevented in the above methods is rheumatoid arthritis, septic shock, erythema nodosum leprosy, septicemia, adult respiratory distress syndrome (ARDS), inflammatory bowel disease (IBD), uveitis and the like.

In another of its aspects, this invention is directed to a compound of formula I or II for use as a pharmaceutical. Additionally, this invention is directed to the use of a compound of formula I or II in the manufacture of a medicament for the treatment or prophylaxis of a neurodegenerative, autoimmune or inflammatory disease or condition.

In another of its method aspects, this invention is directed to a process for preparing a compound of formula II:

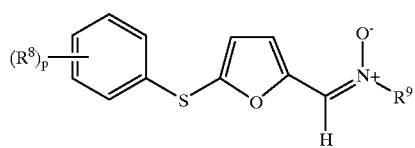

wherein each $R^8$ is independently selected from the group consisting of alkyl, alkoxy, acylamino, trifluoromethoxy and thioalkoxy;

$R^9$ is selected from the group consisting of alkyl and cycloalkyl; and p is an integer ranging from 1 to 3; said process comprising the steps of:

(a) contacting a benzenethiol derivative of the formula:

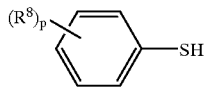

with 2-bromo5-furaldehyde in the presence of a base to provide a thioether carbonyl compound of the formula:

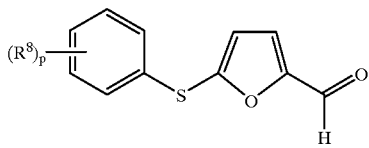

(b) contacting the thioether carbonyl compound with a hydroxylamine derivative of the formula:

to provide a compound of formula II, wherein $R^8$, $R^9$ and p are as defined above.

DETAILED DESCRIPTION OF THE INVENTION

In the thioether furan nitrone compounds of formula I, the substituent may be located at any of the carbon atoms of the furan ring. The furan ring positions are specified herein using conventional furan nomenclature, i.e., the furan ring oxygen atom is the 1 position; the two carbon atoms immediately adjacent the ring oxygen atom are designated the 2 and 5 positions; and the remaining two carbon atoms of the ring are designated the 3 and 4 positions.

In some cases, the thioether furan nitrones of this invention will contain one or more chiral centers. Typically, such compounds will be prepared as a racemic mixture. If desired, however, such compounds can be prepared or isolated as pure stereoisomers, i.e., as individual enantiomers or diastereorners, or as stereoisomer-enriched mixtures. All such stereoisomers (and enriched mixtures) of the thioether furan nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Definitions

When describing the thioether furan nitrones, pharmaceutical compositions and methods of this invention, the following terms have the following meanings unless otherwise specified.

The term "β-amyloid peptide" refers to a 39–43 amino acid peptide having a molecular weight of about 4.2 kD, which peptide is substantially homologous to the form of the protein described by Glenner, et al., *Biochem. Biophys. Res. Commun.*, 120:885–890 (1984), including mutations and post-translational modifications of the normal β-amyloid peptide.

The term "cytokines" refers to peptide protein mediators that are produced by inmmune cells to modulate cellular functions. Examples of cytokines include, interleukin-1β (IL-1β), interleukin-6 (IL-6) and tumor necrosis factor-α (TNFα).

"Acyl" refers to the groups: alkyl-C(O)—, substituted alkyl-C(O)—, cycloalkyl-C(O)— and aryl-C(O)—, where alkyl, substituted alkyl, cycloalkyl, and aryl are as defined herein.

"Acylamino" refers to the group "—NRC(O)R" where each R is independently hydrogen or alkyl.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$CH=CH$_2$), isopropenyl (—C(CH$_3$)=CH$_2$), and the like.

"Substituted alkenyl" refers to alkenyl groups preferably having from 2 to 10 carbon atoms and more preferably 2 to 6 carbon atoms and having at least 1 and preferably from 1–2 sites of alkenyl unsaturation, which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like.

"Alkoxy" refers to "alkyl-O—" groups preferably having from 1 to 12 carbon atoms in the alkyl group, more preferably, 1 to 8 carbon atoms. Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to alkoxy groups which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like. Preferred substituted alkoxy groups include, by way of example, trifluoromethoxy and the like.

"Alkoxycarbonyl" refers to the group "—C(O)OR" where R is alkyl.

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms.

"Substituted alkyl" refers to alkyl groups preferably having from 1 to about 12 carbon atoms, more preferably 1 to 8 carbon atoms and still more preferably 1 to 6 carbon atoms, which are substituted with from 1 to 3 substituents selected from the group consisting of alkoxy, amino, mono- and dialkylamino, acylamino, aminocarbonyl, alkoxycarbonyl, aryloxy, carboxyl, cyano, halo, hydroxy, nitro, thioalkoxy and the like. A preferred substituted alkyl group is the trifluoromethyl group.

"Alkylene" refers to divalent alkylene groups preferably having from 1 to 12 carbon atoms and more preferably 1 to 6 carbon atoms which can be straight chain or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkylenedioxy" refers to "—O-alkylene-O—" groups preferably having from 1 to 10 carbon atoms and more preferably 1 to 6 carbon atoms which can be straight chain or branched. This term is exemplified by groups such as methylenedioxy (—OCH$_2$O—), ethylenedioxy (—OCH$_2$CH$_2$O—) and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH), and the like.

"Aminocarbonyl" refers to the group "—C(O)NRR" where each R is independently hydrogen or alkyl.

"Aralkyl" refers to "aryl-alkylene-" groups preferably having from 1 to 10 carbon atoms in the alkylene moiety and from 6 to 14 carbon atoms in the aryl moiety. Such aralkyl groups are exemplified by benzyl, phenethyl, and the like.

"Aralkyloxy" refers to "aryl-alkylene-O—" groups preferably having from 1 to 10 carbon atoms in the alkylene moiety and from 6 to 14 carbon atoms in the aryl moiety. Such aralkyloxy groups are exemplified by benzyloxy, phenethyloxy, and the like.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 5 substituents, preferably 1 to 3 substituents, selected from the group consisting of alkyl, substituted alkyl, alkenyl, substituted alkenyl, alkynyl, alkylene, alkylenedioxy, cycloalkyl, aralkyl, aryl, alkoxy, substituted alkoxy, aryloxy, aralkyloxy, cycloalkoxy, acyl, acylamino, aminocarbonyl, alkoxycarbonyl, carboxyl, cyano, halo, hydroxy, nitro, sulfonate, thiol, thioalkoxy, thioalkoxycarbonyl and —NRR, where each R is independently selected from hydrogen, alkyl, substituted alkyl or aryl.

"Aryloxy" refers to "—O-aryl" groups wherein aryl is as defined herein.

"Carboxyl" refers to the group "—C(O)OH" and salts thereof

"Cyano" refers to the group "—CN".

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Cycloalkoxy" refers to "—O-cycloalkyl" groups. Such cycloalkoxy groups include, by way of example, cyclopentoxy, cyclohexoxy and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkylalkyl" refers to "cycloalkyl-alkylene-" groups preferably having from 1 to 10 carbon atoms in the alkylene moiety and from 3 to 8 carbon atoms in the cycloalkyl moiety. Such cycloalkylalkyl groups are exemplified by —CH$_2$-cyclopropyl, —CH$_2$-cyclopentyl, —CH$_2$CH$_2$-cyclohexyl, and the like.

"Halo" or "halogen" refers to fluoro, chloro, bromo and iodo.

"Hydroxy" refers to the group "—OH".

"Nitro" refers to the group "—NO$_2$".

"Sulfonate" refers to the group "—SO$_3$H" and salts thereof.

"Thioalkoxy" refers to "alkyl-S—" groups. Preferred thioalkoxy groups include, by way of example, thiomethoxy, thioethoxy, n-thiopropoxy, isothiopropoxy, n-thiobutoxy and the like.

"Thioalkoxycarbonyl" refers to the group "alkyl-S—C(O)—".

"Thiol" refers to the group "—SH".

"Pharmaceutically acceptable salt" refers to pharmaceutically acceptable salts which are derived from a variety of organic and inorganic counter-ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like. The term "pharmaceutically acceptable cation" refers to a pharmaceutically acceptable cationic counter-ion of an acidic functional group. Such cations are exemplified by sodium, potassium, calcium, magnesium, ammonium, tetraalkylammonium cations, and the like.

General Synthetic Procedures

The thioether furan nitrones of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Second Edition, Wiley, New York, 1991, and references cited therein.

In a preferred method of synthesis, the thioether furan nitrones of this invention are prepared by coupling a thioether furan carbonyl compound of formula III:

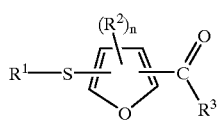

III wherein $R^1$–$R^3$ are as defined above, with a hydroxylamine of formula IV:

IV wherein $R^4$ is as defined above, under conventional reaction conditions.

This coupling reaction is typically conducted by contacting the thioether furan carbonyl compound III with at least one equivalent, preferably about 1.1 to about 2 equivalents, of hydroxylamine IV in an inert polar solvent such as methanol, ethanol, 1,4-dioxane, tetrahydrofuran, dimethyl sulfoxide, dimethylfomiamide and the like. This reaction is preferably conducted at a temperature of from about 0° C. to about 100° C. for about 1 to about 48 hours. Optionally, a catalytic amount of an acid, such as hydrochloric acid, acetic acid, p-toluenesulfonic acid and the like, may be employed in this reaction. Upon completion of the reaction, the thioether furan nitrone of formula I is recovered by conventional methods including precipitation, chromatography, filtration, distillation and the like.

The thioether furan carbonyl compounds of formula III employed in the above-described coupling reaction are either known compounds or compounds that can be prepared from known compounds by conventional procedures. For example, such compounds are readily prepared by reacting a halogen-substituted furan carbonyl compound, such as 5-bromo-2-furaldehyde, with the thiolate anion of a thiol derivative, such as 4-methoxybenzenethiol. Typically, this reaction is conducted by contacting the halogen-substituted furan carbonyl compound with an excess, preferably with about 1.1 to 1.5 equivalents, of the thiol derivative in an inert solvent, such as acetone, 2-butanone and the like, in the presence of a base, such as potassium carbonate. Typically, this reaction is conducted at a temperature ranging from about 0° C. to about 100° C. for about 18 to about 48 hours.

The halogen-substituted furan carbonyl compounds employed in this reaction are either known compounds or compounds which can be prepared from commercially available starting materials using well known procedures and reagents. 5-Bromo-2-furaldehyde is a particularly preferred compound for use in these reactions. Similarly, the thiol derivatives employed in the above-described reaction are commercially available or can be prepared from commercially available starting material using well known procedures and reagents. Preferred thiol derivatives for use in this invention include, but are not limited to, 2-methoxybenzenethiol, 4-methoxybenzenethiol, 4-trifluoromethoxybenzenethicol, 3,5-dimethylbenzenethiol, 4-acetamidobenzenethiol, 4-ethylbenzenethiol and 4-thiomethoxybenzenethiol.

The hydroxylamine compounds of formula IV above are also known compounds or compounds which can be prepared from known compounds by conventional procedures. Typically, the hydroxylamine compounds of formula IV are prepared by reducing the corresponding nitro compound (i.e., $R^5$—$NO_2$, wherein $R^5$ is as defined above) using a suitable reducing agent such as activated zinc/acetic acid, activated zinc/ammonium chloride or an aluminum/mercury amalgam. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc reagents or an ether/water mixture in the case of the aluminum amalgams. Aliphatic nitro compounds (in the form of their salts) can also be reduced to hydroxylamines using borane in tetrahydrofuran. Since some hydroxylamines have limited stability, such compounds are generally prepared immediately prior to reaction with the thioether furan carbonyl compound of formula III.

Preferred hydroxylamines for use in this invention include, but are not limited to, N-isopropylhydroxylamine, N-n-propylhydroxylamine, N-n-butylhydroxylamine, N-tert-butylhydroxylamine, N-cyclopentylhydroxylamine, N-cyclohexylhydroxylamine, N-2,4,4-trimethylpent-2-ylhydroxylamine and the like.

Pharmaceutical Compositions

When employed as pharmaceuticals, the compounds of this invention are typically administered in the form of a pharmaceutical composition. Such compositions can be prepared using procedures well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patients symptoms, and the like.

The pharmaceutical compositions of this invention can be administered by a variety of routes including oral, rectal, transdermal, subcutaneous, intravenous, intramuscular, intranasal, topical and the like. Depending on the intended route of delivery, the compounds of this invention are preferably formulated as either injectable or oral compositions.

Pharmaceutical compositions for oral administration can take the form of bulk liquid solutions or suspensions, or bulk powders. More commonly, however, such compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the active compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

The above-described components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active compound per tablet) in a tablet press.

Formulation 2—Capsules

A compound of formula I is admixed as a dry powder with a starch diluent in an approximate 1:1 weight ratio. The mixture is filled into 250 mg capsules (125 mg of active compound per capsule).

Formulation 3—Liquid

A compound of formula I (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate(10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active compound) in a tablet press.

Formulation 5—Injection

The compound of formula I is dissolved in a buffered sterile saline injectable aqueous medium to a concentration of approximately 5 mg/ml.

Compound Utility

The compounds of this invention have been discovered to inhibit the formation of $A\beta(1-42)$ beta-pleated sheets and/or inhibit the release of cytokines, such as IL-1$\beta$. As previously discussed, the formation of $A\beta(1-42)$ beta-pleated sheets is associated with neurodegenerative conditions, such as Alzheimer's disease, and/or inflammatory conditions. Additionally, elevated levels of cytokines are associated with neurodegenerative, autoimmune and/or inflammatory conditions. Accordingly, the compounds and pharmaceutical compositions of this invention find use as therapeutics for preventing and/or treating neurodegenerative, autoimmune and inflammatory conditions in mammals including humans.

Among the conditions which may be treated and/or prevented with the compounds of formula I are neurodegenerative conditions, such as Alzheimer's disease, Parkinson's disease, HIV-dementia and the like; autoimmune conditions, such as systemic lupus, multiple sclerosis and the like; and inflammatory conditions, such as inflammatory bowel disease (IBD), rheumatoid arthritis, septic shock, erythema nodosum leprosy, septicemia, uveitis, adult respiratory distress syndrome (ARDS) and the like.

Additionally, since the compounds of this invention have been discovered to effectively inhibit the release of cytokines, such a IL-1$\beta$, IL-6 and TNF$\alpha$, and the neuronal damage induced by cytokines, such as IL-1$\beta$, such compounds are useful for treating diseases characterized by an overproduction or a dysregulated production of cytokines, particularly IL-1$\beta$, IL-6 and TNF$\alpha$, including many autoimmune and/or inflammatory conditions.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels.

The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.1 to about 20 mg/kg of the compound of formula I, with preferred doses each providing from about 0.1 to about 10 mg/kg and especially about 1 to about 5 mg/kg.

When used to prevent the onset of a neurodegenerative, autoimmune or inflammatory condition, the compounds of this invention will be administered to a patient at risk for developing the condition, typically on the advice and under the supervision of a physician, at the dosage levels described above. Patients at risk for developing a particular condition generally include those having a family history of the condition, or those who have been identified by genetic testing or screening to be particularly susceptible to developing the condition.

The compounds of this invention can be administered as the sole active agent or they can be administered in combination with other agents, including other active nitrone derivatives.

The compounds of this invention are also useful as analytical reagents, i.e. as spin traps, for detecting unstable free radicals using electron spin resonance (ESR) spectroscopy and related techniques. When used as analytical reagents, the nitrone compounds of this invention are typically contacted with the radical to be studied in solution and an ESR spectrum generated in a conventional manner. In particular, the compounds of this invention may be used to detect and identify free radicals in biological systems. Any ESR spectrometer, such as a JEOL JES-FE3XG spectrometer, may be employed in these experiments. Typically, the solution containing the spin-trap will be deoxygenated by, for example, bubbling argon or nitrogen through the solution before the ESR experiment is conducted. Preferably, an excess of the nitrone is used in such ESR experiments.

The actual experimental procedures employed in the spin-trapping experiment will depend on a number of factors, such as the manner of radical production, the inertness of the solvent and reagents with respect to the spin trap, the lifetime of the spin adduct and the like. Spin trapping procedures are well known in the art and the exact procedure employed can be determined by those skilled in the art. Typical procedures and apparatus for conducting spin trapping experiments are described, for example, in C. A. Evans, "Spin Trapping", *Aldrichimica Acta,* (1979), 12(2), 23–29, and references cited therein.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.

| | | |
|---|---|---|
| bd | = | broad doublet |
| bs | = | broad singlet |
| d | = | doublet |
| dd | = | doublet of doublets |
| dec | = | decomposed |
| dH$_2$O | = | distilled water |
| ELISA | = | enzyme-linked immuno-sorbent assay |
| EtOAc | = | ethyl acetate |

-continued

| | | |
|---|---|---|
| EtOH | = | ethanol |
| FBS | = | fetal bovine serum |
| g | = | grams |
| h | = | hours |
| Hz | = | hertz |
| IL-1β | = | interleukin-1β |
| IL-6 | = | interleukin-6 |
| L | = | liter |
| LPS | = | lipopolysaccharide |
| m | = | multiplet |
| min | = | minutes |
| M | = | molar |
| MeOH | = | methanol |
| mg | = | milligram |
| MHz | = | megahertz |
| mL | = | milliliter |
| mmol | = | millimole |
| m.p. | = | melting point |
| N | = | normal |
| q | = | quartet |
| quint. | = | quintet |
| s | = | singlet |
| t | = | triplet |
| THF | = | tetrahydrofuran |
| ThT | = | thioflavin T |
| tlc | = | thin layer chromatography |
| TNFα | = | tumor necrosis factor-α |
| μg | = | microgram |
| μL | = | microliter |
| UV | = | ultraviolet |

In the examples below, all temperatures are in degrees Celsius (unless otherwise indicated). Example A–C describe the synthesis of intermediates useful for preparing thioether furan nitrones; Examples 1–18 describe the synthesis of various thioether furan nitrones of this invention; and Examples 19–23 describe the testing of such compounds.

Example A

Synthesis of N-tert-Butylhydroxylamine

Zinc dust (648 g) was added in portions to a cooled mixture of 2-methyl-2-nitropropane (503 g) and ammonium chloride (207 g) in deionized water (6 L) at such a rate so as to maintain the temperature below 18° C. The reaction mixture was stirred mechanically for 15 hours and then filtered. The solid was washed with hot water (1.75 L). The combined filtrate was saturated with potassium carbonate (4.6 Kg) and extracted with ethyl acetate (2×1300 mL). The organic solution was dried over anhydrous sodium sulfate, filtered and rotary evaporated to give the title compound (329 g, 75.7% yield) as white crystals. This material was used without further purification.

Spectroscopic data were as follows:
$^1$H NMR (CDCl$_3$, 270 MHz) δ=1.090 (s, 3 CH$_3$).

Example B

Synthesis of N-Isopropylhydroxylamine

Using the procedure of Example A above and 2-nitropropane, the title compound was prepared. The crude hydroxylamine product was used without further purification.

Example C

Synthesis of N-Cyclohexylhydroxylamine

Using the procedure of Example A above and nitrocyclohexane, the title compound can be prepared. Alternatively, N-cyclohexylhydroxylamine hydrochloride may be purchased commercially from Aldrich Chemical Company, Inc., Milwaukee, Wis. USA and neutralized with a base, such as potassium carbonate, to provide the title compound.

Example 1

Synthesis of α-[2-(4-Methoxyphenylthio)-5-furyl]-N-tert-butylnitrone

Step A—Synthesis of 2-(4-Methoxyphenylthio)-5-furaldehyde

To a solution of 2-bromo-5-furaldehyde (20.0 g, 114.29 mmol) in acetone (200 mL) was added 4-methoxybenzenethiol (15.5 mL, 125.75 mmol) and potassium carbonate (20 g). The reaction mixture was stirred at room temperature for 19 hours, and then filtered and concentrated on a rotary evaporator. The solid obtained was recrystallized from hexanes (300 mL) and ethyl acetate (50 mL) to give yellowish crystals (24.50 g).

Step B—Synthesis of α-[2-(4Methoxyphenylthio)-5-furyl]-N-tert-butylnitrone 2-(4-Methoxyphenylthio)-5-furaldehyde (24.50 g) was mixed with N-tert-butylhydroxylamine (15.0 g, 168.16 mmol), molecular sieves (100 g) and silica gel (20 g) in $CDCl_3$ (500 mL). The mixture was refluxed overnight under argon gas, and then filtered and concentrated on a rotary evaporator. The residue was recrystallized from hexanes (435 mL) to afford the title compound as yellowish crystals (27.52 g, yield 78.8%), m.p. 91.7° C. ($R_f$=0.15 on a silica gel plate using hexanes/EtOAc, 2:1, v:v, as the eluant).

Spectroscopic data were as follows:

IR (KBr, $cm^{-1}$): 2973.9 (CH), 1633.8 (C=N), 1593.5 (benzene ring), 1247.1 (Ar—O) and 1119.7 (N—O).

$^1H$ NMR ($CDCl_3$, 270 MHz) δ=7.732 (1H, d, J=3.5 Hz, furan H), 7.654 (1H, s, nitronyl H), 7.270 (2H, d, J=8.9 Hz, benzene 2H), 6.812 (2H, d, J=8.9 Hz, benzene 2H), 6.669 (1H, d, J=3.5 Hz, furan H), 3.755 (3H, s, $CH_3O$) and 1.529 (9H, s, $(CH_3)_3C$.

$^{13}C$ NMR ($CDCl_3$, 270 MHz) δ=159.492, 150.279, 147.002, 132.112, 124.481, 121.119, 119.034, 116.345, 114.947, 70.050, 55.443, and 28.132.

Example 2

Synthesis of α-[2-(2-Methoxyphenylthio)-5-furyl]-N-tert-butylnitrone

The title compound was prepared according to the procedure described in Example 1 using 2-methoxybenzenethiol and N-tert-butylhydroxylamine. The title compound was isolated in 7.8% yield as a yellowish solid, m.p. 124.8° C. ($R_f$=0.19 on a silica gel plate using hexanes/EtOAc, 2:1, v:v, as the eluant).

Spectroscopic data were as follows:

IR (KBr, $cm^{-1}$): 2976.0 (CH), 1632.0 (C=N), 1579.1 (benzene ring), 1241.8 (Ar—O) and 1121.3 (N—O).

$^1H$ NMR ($CDCl_3$, 270 MHz): δ=7.810 (1H, d, J=3.3 Hz, furan H), 7.713 (1H, s, nitronyl H), 7.190–7.126 (1H, m, J=8.9 Hz, benzene H), 6.855 (1H, d, J=3.3 Hz, furan H), 6835–6.811 (3H, m, benzene 3H), 3.880 (3H, s, $CH_3O$), and 1.555 (9H, s, $(CH_3)_3C$).

$^{13}C$ NMR ($CDCl_3$, 270 MHz): δ=155.909, 151.012, 144.022, 128.361, 127.735, 124.137,121.837, 121.180, 116.406, 110.898,70.203,56.001 and 28.148.

Example 3

Synthesis of α-[2-(4-Methoxyphenylthio)-5-furyl]-N-cyclohexylnitrone

The title compound was prepared according to the procedure described in Example 1 using 4-methoxybenzenethiol and N-cyclohexylhydroxylamine. The title compound was isolated in 63.6% yield as white crystals, m.p. 115.5° C. ($R_f$=0.18 on a silica gel plate using hexanes/EtOAc, 2:1, v:v, as the eluant).

Spectroscopic data were as follows:

IR (KBr, $cm^{-1}$): 2935 (CH), 1633 (C=N), 1590 (benzene ring), 1247 (Ar-O) and 1137 (N—O).

$^1H$ NMR ($CDCl_3$, 270 MHz): δ=7.73 (1H, d, J=3.5 Hz, furan H), 7.53 (1H, s, nitronyl H), 7.29 (2H, d, J=8.8 Hz, benzene 2H), 6.83 (2H, d, J=8.8 Hz, benzene 2H), 6.67 (1H, d, J=3.5 Hz, furan H), 3.84–3.72 (1H, m, N—CH), 3.78 (3H, s, MeO), 2.08–2.04 (2H, m, cyclohexyl 2H), 1.93–1.78 (4H, m, cyclohexyl 4H), 1.72–1.67 (1H, m, cyclohexyl H), 1.43–1.19 (3H, m, cyclohexyl 3H).

$^{13}C$ NMR($CDCl_3$, 270 MHz): δ=159.35, 149.52, 146.80, 132.02, 124.25, 122.77, 118.67, 116.31, 114.77, 74.12, 55.26, 31.06, 24.87.

Example 4

Synthesis of α-[2-(4Trifluoromethoxyphenylthio)-5-furyl]-N-tert-butylnitrone

The title compound was prepared according to the procedure described in Example 1 using 4-trifluoromethoxybenzenethiol and N-tert-butylhydroxylamine. The title compound was isolated in 46.3% yield as slightly yellowish crystals, m.p. 118.0° C. ($R_f$=0.39 on a silica gel plate using hexanes/EtOAc, 2:1, v:v, as the eluant).

Spectroscopic data were as follows:

IR (KBr, $cm^{-1}$): 2980 (CH), 1633 (C=N), 1570 (benzene ring), 1287 (Ar-O) and 1159 (N—O).

$^1H$ NMR ($CDCl_3$, 270 MHz): δ=7.82 (1H, d, J=3.5 Hz, furan H), 7.72 (1H, s, nitronyl H), 7.22 (2H, d, J=8.9 Hz, benzene 2H), 7.14 (2H, d & q, $J_d$=8.9 Hz, $J_q$=1.0 Hz benzene 2H), 6.87 (1H, d, J=3.5 Hz, furan H), 1.57 (9H, s, tert-butyl).

$^{13}C$ NMR ($CDCl_3$, 270 MHz): δ=151.15, 148.02, 143.75, 133.86, 129.45, 121.78, 121.58, 120.81, 120.33 (q, J=257.6 Hz), 116.07, 70.29, 28.02.

Example 5

Synthesis of α-[2-(3,5-Dimethylphenylthio)-5-furyl]-N-tert-butylnitrone

The title compound was prepared according to the procedure described in Example 1 using 3,5-dimethylbenzenethiol and N-tert-butylhydroxylamine. The title compound was isolated in 52.1% yield as yellowish crystals, m.p. 80.3° C. ($R_f$=0.37 on a silica gel plate using hexanes/EtOAc, 2:1, v:v, as the eluant).

Spectroscopic data were as follows:

IR (KBr, $cm^{-1}$): 2968 (CH), 1598 (C=N), 1575 (benzene ring) and 1117 (N—O).

$^1H$ NMR ($CDCl_3$, 270 MHz): δ=7.81 (1H, d, J=3.5 Hz, furan H), 7.72 (1H, s, nitronyl H), 6.83 (1H, s, benzene 3H), 6.82 (1H, d, furan H overlapped with benzene H), 2.25 (6H, s, 2 Me), 1.56 (9H, s, tert-butyl).

$^{13}C$ NMR ($CDCl_3$, 270 MHz): δ=150.61, 145.13, 138.89, 134.28,128.72, 125.91, 121.06, 120.87, 116.16, 70.03, 27.99, 21.14.

Example 6

Synthesis of α-[2-4Acetamidophenylthio)-5-furyl]-N-tert-butylnitrone

The title compound was prepared according to the procedure described in Example 1 using 4-acetamidobenzenethiol and N-tert-butylhydroxylamine. The title compound was isolated in 18.2% yield as yellowish crystals, m.p. 140.3° C. ($R_f$=0.37 on a silica gel plate using EtOAc as the eluant).

Spectroscopic data were as follows:

IR (KBr, cm$^{-1}$): 2979 (CH), 1673 (C=O), 1639 (C=N), 1592 (benzene ring) and 1113 (N—O).

$^1$H NMR (CDCl$_3$, 270 MHz): δ=8.19 (1H, broad s, NH), 7.76 (1H, d, J=3.5 Hz, furan H), 7.71 (1H, s, nitronyl H), 7.46 (2H, d, J=8.7 Hz, benzene 2H), 7.20 (2H, d, J=8.7 Hz, benzene 2H), 6.75 (1H, d, J=3.5 Hz, furan H), 2.14 (3H, s, CH$_3$), 1.56 (9H, s, tert-butyl).

$^{13}$C NMR (CDCl$_3$, 270 MHz): δ=168.72, 150.29, 145.81, 137.50, 130.06, 128.86, 121.28, 120.65, 119.95, 116.31, 70.06, 27.98, 24.39.

Example 7

Synthesis of α-[2-(4-Ethylphenylthio)-5furyl]-N-tert-butylnitrone

The title compound was prepared according to the procedure described in Example 1 using 4-ethylbenzenethiol and N-tert-butylhydroxylamine. The title compound was isolated in 63.7% yield as white crystals, m.p. 123.5° C. ($R_f$=0.32 on a silica gel plate using hexanes/EtOAc, 2:1, v:v, as the eluant).

Spectroscopic data were as follows:

IR (KBr, cm$^{-1}$): 2965 (CH), 1634 (C=N), 1571 (benzene ring), 1204 (C—N) and 1119 (N—O).

$^1$H NMR (CDCl$_3$, 270 MHz): δ=7.79 (1H, d, J=3.5 Hz, furan H), 7.70 (1H, s, nitronyl H), 7.18 (2H, d, J=8.4 Hz, benzene 2H), 7.11 (2H, d, J=8.4 Hz, benzene 2H), 6.78 (1H, d, J=3.5 Hz, furan H), 2.60 (2H, q, CH$_2$), 1.57 (9H, s, tert-butyl), 1.20 (3H, t, CH$_3$).

$^{13}$C NMR (CDCl$_3$, 270 MHz): δ=150.47, 145.51, 143.32, 131.23, 128.89, 128.72, 120.93, 120.26, 116.11, 69.96, 28.29, 27.96, 15.37.

Example 8

Synthesis of α-[2-(4-Thiomethoxyphenylthio)-5furyl]-N-teri-butylnitrone

The title compound was prepared according to the procedure described in Example 1 using 4-thiomethoxybenzenethiol and N-tert-butylhydroxylamine. The title compound was isolated in 26.1% yield as yellowish crystals, m.p. 120.4° C. ($R_f$=0.27 on a silica gel plate using hexanes/EtOAc, 2:1, v:v, as the eluant).

Spectroscopic data were as follows:

IR (KBr, cm$^{-1}$): 2979 (CH), 1630 (C=N), 1579 (benzene ring), 1210 (C—N) and 1119 (N—O).

$^1$H NMR (CDCl$_3$, 270 MHz): δ=7.79 (1H, d, J=3.5 Hz, furan H), 7.70 (1H, s, nitronyl H), 7.16 (4H, s, benzene 4H), 6.79 (1H, d, J=3.5 Hz, furan H), 2.44 (3H, s, MeS), 1.56 (9H, s, tert-butyl).

$^{13}$C NMR (CDCl$_3$, 270 MHz): δ=150.61, 145.00, 137.79, 130.82, 129.35, 127.13, 120.87, 120.42, 116.08, 70.04, 27.96, 15.72.

Example 9

Synthesis of α-[2-(4-Methoxyphenylthio)-5-furyl]-N-isopropylnitrone

The title compound was prepared according to the procedure described in Example 1 using 4-methoxybenzenethiol and N-isopropylhydroxylamine. The title compound was isolated in 62.0% yield as slightly yellowish crystals, m.p. 93.3° C. ($R_f$=0.17 on a silica gel plate using hexanes/EtOAc, 2:1, v:v, as the eluant).

Spectroscopic data were as follows:

IR (KBr, cm$^{-1}$): 2979 (CH), 1636 (C=N), 1577 (benzene ring), 1247 (Ar—O) and 1143 (N—O).

$^1$H NMR (CDCl$_3$, 270 MHz): δ=7.74 (1H, d, J=3.5 Hz, furan H), 7.55 (1H, s, nitronyl H), 7.29 (2H, d, J=8.9 Hz, benzene 2H), 6.83 (2H, d, J=8.9 Hz, benzene 2H), 6.68 (1H, d, J=3.5 Hz, furan H), 4.14 (1H, septet, J=6.6 Hz, N—CH), 3.77 (3H, s, MeO), 1.46 (6H, d, J=6.6 Hz, 2 Me).

$^{13}$C NMR (CDCl$_3$, 270 MHz): δ=159.35, 149.40, 146.88, 132.06, 124.19, 122.56, 118.68, 116.37, 114.78, 66.47, 55.27, 20.76.

Example 10

Synthesis of α-[2-(4-Trifluoromethoxyphenylthio)-5-furyl]-N-cyclohexylnitrone

The title compound was prepared according to the procedure described in Example 1 using 4-trifluoromethoxybenzenethiol and N-cyclohexylhydroxylamine. The title compound was isolated in 51.8% yield as white crystals, m.p. 145.8° C. ($R_f$=0.35 on a silica gel plate using hexanes/EtOAc, 2:1, v:v, as the eluant).

Spectroscopic data were as follows:

IR (KBr, cm$^{-1}$): 2935 (CH), 1636 (C=N), 1576 (benzene ring), 1289 (Ar—O), 1215 (C—F) and 1162 (N—O).

$^1$H NMR (CDCl$_3$, 270 MHz): δ=7.80 (1H, d, J=3.3 Hz, furan H), 7.59 (1H, s, nitronyl H), 7.22 (2H, d, J=8.7 Hz, benzene 2H), 7.12 (2H, d & q, $J_d$=8.7 Hz & $J_q$=0.7 Hz, benzene 2H), 6.86 (1H, d, J=3.3 Hz, furan H), 3.1 (1H, tt, J=11.4 & 3.9 Hz, N—CH), 2.09–2.06 (2H, m, cyclohexyl 2H), 1.99–1.81 (4H, m, cyclohexyl 4H), 1.72–1.68 (1H, m, cyclohexyl H), 1.43–1.14 (3H, m, cyclohexyl 3H).

$^{13}$C NMR (CDCl$_3$, 270 MHz): δ=150.51, 147.95, 143.62, 133.78, 129.42, 122.65, 121.71, 121.42, 120.27, 116.18, 74.38, 31.08, 24.85

Example 11

Synthesis of α-[2-(4Methoxyphenylthio)-5-furyl]-N-n-butylnitrone

The title compound was prepared according to the procedure described in Example 1 using 4-methoxybenzenethiol and N-n-butylhydroxylamine. The title compound was isolated in 44.7% yield as yellowish crystals, m.p. 44.6° C. ($R_f$=0.17 on a silica gel plate using hexanes/EtOAc, 2:1, v:v, as the eluant).

Spectroscopic data were as follows:

IR (KBr, cm$^{-1}$): 2959 (CH), 1637 (C=N), 1591 (benzene ring), 1247 (Ar—O) and 1143 (N—O).

$^1$H NMR (CDCl$_3$, 270 MHz): δ=7.74 (1H, d, J=3.5 Hz, furan H), 7.49 (1H, s, nitronyl H), 7.30 (2H, d, J=8.9 Hz, benzene 2H), 6.84 (2H, d, J=8.9 Hz, benzene 2H), 6.67 (1H, d, J=3.5 Hz, furan H), 3.87 (2H, t, J=7.1 Hz, N—CH), 3.80 (3H, s, MeO), 1.98–1.87 (2H, m, CH$_2$), 1.45–1.31 (2H, m, CH$_2$), 0.95 (3H, t, J=7.3 Hz, CH$_3$).

$^{13}$C NMR (CDCl$_3$, 270 MHz): δ=159.44, 149.16, 147.21, 132.26, 124.76, 124.04, 118.50, 116.52, 114.81, 66.49, 55.30, 29.56, 19.62 and 13.50.

Example 12

Synthesis of α-[2-(4-Methoxyphenylthio)5-furyl]-N-n-propylnitrone

The title compound was prepared according to the procedure described in Example 1 using 4-methoxybenzenethiol and N-n-propylhydroxylamine. The title compound was isolated in 76.6% yield as slightly yellowish crystals, m.p. 63.0° C. ($R_f$=0.17 on a silica gel plate using hexanes/EtOAc, 2:1, v:v, as the eluant).

Spectroscopic data were as follows:

IR (KBr, cm$^{-1}$): 2966 (CH), 1630 (C=N), 1591 (benzene ring), 1245 (Ar—O) and 1144 (N—O).

$^1$H NMR (CDCl$_3$, 270 MHz): δ=7.74 (1H, d, J=3.3 Hz, furan H), 7.49 (1H, s, nitronyl H), 7.31 (2H, d, J=8.9 Hz, benzene 2H), 6.84 (2H, d, J=8.9 Hz, benzene 2H), 6.67 (1H, d, J=3.3 Hz, furan H), 3.83 (2H, t, J=7.2 Hz, N—CH), 3.78 (3H, s, MeO), 1.98 (2H, sextet, CH$_2$), 0.97 (3H, t, J=7.2 Hz, CH$_3$).

$^{13}$C NMR (CDCl$_3$, 270 MHz): δ=159.48, 149.15, 147.27, 132.29, 124.87, 124.06, 118.50, 116.57, 114.83, 67.29, 55.31, 20.96 and 10.89.

Using the appropriate starting materials and the procedures described herein or those available to one skilled in the art, the following additional compounds were prepared:

| Ex. | Compound | Melting Point |
| --- | --- | --- |
| 13 | α-[2-(4-trifluoromethoxyphenylthio)-5-furyl]-N-isopropylnitrone | 92.4° C. |
| 14 | α-[2-(4-trifluoromethoxyphenylthio)-5-furyl]-N-n-propylnitrone | 71.0° C. |
| 15 | α-[2-(4-methoxyphenylthio)-5-furyl]-N-2,4,4-trimethylpent-2-ylnitrone | 94.8° C. |
| 16 | α-[2-(4-trifluoromethoxyphenylthio)-5-furyl]-N-2,4,4-trimethylpent-2-ylnitrone | 66.9° C. |
| 17 | α-[2-(4-methoxyphenylthio)-5-furyl]-N-cyclopentylnitrone | 111.5° C. |
| 18 | α-[2-(4-trifluoromethoxyphenylthio)-5-furyl]-N-cyclopentylnitrone | 142.7° C. |

Example 19

Electron Spin Resonance (ESR) Study

Using the following procedures, the thioether furan nitrones of this invention to trap free radicals could be shown to trap free radicals using ESR spin trapping techniques. For additional experimental details, see, for example, K. R. Maples et al., "In Vivo Detection of Free Radical Metabolites", *Free Radicals in Synthesis and Biology* (F. Minisci, ed.) pp. 423–436 (Kluwer Academic Publishers, Boston, 1989); and J. A. DeGray et al., "Biological Spin Trapping", *Electron Spin Resonance* 14:246–300 (1994). In this experiment, a t-butyl hydroperoxide/ferrous iron free radical generating system is used. This free radical generating system produces t-butyl-alkoxyl radicals, t-butyl-peroxyl radicals, and methyl radicals. If the thioether furan nitrones of this invention are capable of trapping any of these radicals to form a stable radical adduct, such radical adducts should be detectable by ESR spectroscopy.

To 490 µl of a 100 mM solution of the thioether furan nitrone in water is added 5 µl of 100 mM ferrous sulfate. The reaction is initiated by the addition of 5 µl of 100 mM 1-butyl hydroperoxide. The final concentrations of reagents are 1 mM ferrous iron, 1 mM t-butyl hydroperoxide and 98 mM of the nitrone compound in water. Once mixed, the solution is quickly transferred into a quartz flat cell and this cell is placed in the cavity of a Bruiker ESP 300 ESR spectrometer, and scanned within 5 minutes of mixing. ESR spectrometer settings are: 3480 G center field, 200 G field width, 480 seconds sweep time, 9.76 GHz frequency, 10 dB power, 1.6×10$^5$ receiver gain, 0.200 G modulation amplitude, 0.320 second time constant, and 270° phase. The resulting ESR spectrum would show that the thioether furan nitrone is effective at trapping free radicals and that such compounds can be used as analytical reagents for ESR applications.

Example 20

Inhibition of Aβ Beta-Pleated Sheet Formation

The deposition of amyloid β-peptide (Aβ) is associated with the development of Alzheimer's disease. See, for example, G. G. Glenner et al. (1984) *Biochem. Biophys. Res. Commun.*, 120:885–890; and R. E. Tanzi (1989) *Ann. Med.*, 21:91–94. Accordingly, compounds which effectively disrupt the formation of Aβ(1–40) or Aβ(1–42) beta-pleated sheets are potentially useful for preventing and/or reversing such amyloid deposits. Thioflavin T (ThT) is known to rapidly associate with beta-pleated sheets, particularly the aggregated fibrils of synthetic Aβ(1–42). This association gives rise to an excitation maximum at 440 nm and to an emission at 490 nm. In this experiment, the ability of certain thioether furan nitrones of formula I above to inhibit the association of ThT with synthetic Aβ(1–42) is demonstrated by measuring changes in fluorescence.

The experiments were performed using a CytoFluor II fluorescence plate reader having the following parameters:

| | |
| --- | --- |
| Filters: | Excitation 440 nm/20 |
| | Emission 490 nm/40 |
| Gain: | 75 |
| Cycle to Cycle Time: | 30 min |
| Run Time: | 720 min (24 cycles) or dependent on experimental design |
| Plate: | 96 well |

Into each well was aliquoted 95 µl of ThT (3 µM) prepared in PBS (pH 6.0), 2 µL of the compound to be tested (10 µM) prepared with 0.05% of methylcellulose in PBS (pH 6.0), and 3 µL of Aβ(1–42)(3 µg) prepared with dH$_2$O. The fluorescence measurement began when the Aβ(1–42) was added and continued for a total of 12 hours. The percent inhibition of beta-pleated sheet formation was calculated from the relative fluorescence unit difference between aggregation in the presence and in the absence of the test compounds. Inhibition of Aβ(1–42) beta-pleated sheet formation by at least 30% compared to the controls is considered significant in this test. The results of these in vitro tests are described below.

Example 21

Protection Against Aβ(25–35)-Induced Neuronal Cell Loss

Patients with Alzheimer's disease are known to suffer a progressive loss of neuronal cells. See, for example, P. J. Whitehause et al., (1982) *Science*, 215:1237–1239. In this experiment, the ability of certain thioether furan nitrones of formula I above to protect against Aβ(25–35)-induced neuronal cell loss is demonstrated. Sprague Dawley rat hippocampus of 18-day-gestation embryos was excised and then dissociated by trituration to prepare primary neuronal cultures. Cells (3×10$^5$) were plated on 35 mm poly-D-lysine-coated plates containing Eagle's minimum essential medium supplemented with 10% fetal bovine serum. After 3–5 hours, the original medium was removed and replaced with 1 mL of fresh medium. Cultures were maintained at 37° C. in a 5% CO$_2$/95% air humidified incubator. Glial growth is observed as a monolayer under neurons.

To the cells (7 DIV) was added 30 μM of Aθ(25–35) dissolved in dH$_2$O (stored at −20° C.) and 100 μM of the test compound in 1% methylcellulose Controls were also conducted without the test compound. The percentage of morphologically viable neurons was determined by counting the number of viable neurons after 96 hours treatment (three regions/well, n=6 wells). Inhibition of Aβ(25–35)-induced neuronal cell loss by at least 30% compared to the controls is considered significant in this test. The results of these in vitro tests are described below.

Example 22

Reduction of β-Amyloid-Induced Increased Release of Interleukin-1β

In this experiment, the ability of certain thioether furan nitrones of formula I above to reduce the β-amyloid-induced increased release over LPS alone of interleukin-1β(IL-1β) is demonstrated. THP-1 cells, a human monocyte cell line from American Type Culture Collection, were grown in RPMI-1640 medium plus 10% fetal bovine serum (FBS, not heat-inactivated) in T-flasks. The medium was changed every two days by spinning down the cells (800 rpm, 5 minutes) and adding the same fresh medium. Alternatively, the cultures were maintained by supplantation with fresh medium. The cultures were maintained at a cell concentration ranging from between 1×10$^5$ and 1×10$^6$ cells/mL. Because sera may contain unknown factors which can affect macrophage/monocyte IL-1 production, the FBS was reduced to 5% for 24 hours. The FBS was further reduced to 2% over two days prior to starting each experiment. The cells were collected by centrifugation and resuspended in media containing 2% FBS. Cell numbers were calculated and cells were plated on 24-well plates (3×10$^5$ cells/0.6 mL/well). Cells were then treated with LPS (0.5 μ/mL) alone or in combination with Aβ peptides (5 μM). When determining the effect of the test compounds on IL-1β release, 100 μM of the test compound was added with the LPS and Aβ(25-35) and this mixture was incubated for 48 hours prior to performing ELISA.

IL-1β secretions into medium by LPS-stimulated THP-1 cells, in the presence or absence of amyloid peptides and a test compound, were assayed with a commercially available ELISA kit (R & D Systems). Briefly, a microtiter plate coated with a murine monoclonal antibody to human IL-1β was supplied by the manufacturer. Standards and samples were pipetted into the wells and any IL-1β present was bound by the immobilized antibody. Unbound proteins were washed away and a horseradish peroxidase-linked polyclonal antibody specific for IL-1β was added to the wells to "sandwich" the IL-1β bound in the initial step. After washing to remove any unbound antibody-enzyme reagent, a substrate solution (1:1 hydrogen peroxide:tetramethylbenzidine, v/v) was added to the wells and color developed in proportion to the amount of IL-1β bound in the initial step. Color development was stopped with 2 N sulfuric acid and the optical density of the standard and the test samples was measured at 450 nm. The amount of IL-1β present in the samples were calculated based upon a standard curve. Assays were run in quadruplicate wells. Inhibition of β-amyloid-induced increase release of interleukin-1β by at least 30% compared to controls is considered significant in these tests. The results of these in vitro tests are described below.

Example 23

Reduction of IL-1β-Induced Cell Toxicity

In this experiment, the ability of certain thioether furan nitrones of formula I to reduce cytokine-induced rat cortical neuronal cell damage is demonstrated. Sprague-Dawley embryos were rapidly removed from the mother rats and placed in cold calcium- and magnesium-free Hank's balanced salt solution (HBSS) for further dissection. The cortical cell cultures, containing both neurons and glia, were prepared by plating fetal rat cortical cells on a confluent bed of cortical glia. Mixed glial cultures were prepared from the postnatal one day old rat cortex. To prepare such cultures, the cortex was removed aseptically and blood vessels and membranes were carefully removed, and dissociated in cold calcium- and magnesium-free HBSS buffer. The dissociated cells were plated on 24 well plates (about 1.5 hemispheres per plate), and grown for 2.5 weeks at 37° C. and 5% CO$_2$ in medium consisting of DMEM/F 12, 10% heat-inactivated FBS and 100 units/mL penicillin/100 μg/mL streptomycin.

To establish a neuronal component, rat cerebral cortex of 16-day gestation embryos were dissected free and incubated in HBSS containing 0.1% trypsin at 37° C. for 30 minutes. Tissue was then suspended in plating medium consisting of DMEM/F12, 10% heat-inactivated FBS and 100 units/mL penicillin/100 μg/mL streptomycin. After trituration, cells are seeded onto glial cultures at a density of 5.0×10$^5$/mL/well. Cultures were incubated at 37° C. in a humidified atmosphere containing 5% CO$_2$, Non-neuronal cells are inhibited at 5 days in vitro (DIV) by addition of 10 μM cytosine arabinoside for 3 days. Experiments were conducted at 8 DIV neuronal and 25 DIV glial cultures in the same medium without FBS.

Into each well was added 1 mL of medium containing 200 units/mL of recombinant mouse IL-1β (Genzyme). The compound to be tested (10 μL) in 1% methyl cellulose (100 μM final concentration) was added immediately to each well. Control wells contained IL-1β and 1% methyl cellulose. Cultures were incubated at 37° C. in a humidified atmosphere containing 5% CO$_2$ for 48 hours. Neuronal injury was estimated in all experiments by examination of cultures with phase-contrast microscopy and was quantified by measurement of cytosolic lactate dehydrogenase (LDH) release into the cell medium. Reduction of LDH release by at least 30% compared to controls is considered significant in these tests. The results of these in vitro tests are described below.

In vitro Test Results

The compounds prepared in Examples 1–17 were tested in at least one of the above described in vitro tests (the compound of Example 18 was not tested). Each of the compounds of Examples 1–17 inhibited Aβ(1–42) beta-pleated sheet formation and/or β-amyloid-induced increase release of interleukin-1β and/or IL-1β-induced cell toxicity by at least 30% compared to the controls, except for the compound of Example 7 which was not tested in either the β-amyloid-induced increase release of interleukin-1β or the 1β-induced cell toxicity tests. The compound of Example 7 is expected to inhibit the β-amyloid-induced increase release of interleukin-1β and/or the IL-1β-induced cell toxicity by at least 30% compared to the controls.

From the foregoing description, various modifications and changes in the compositions and methods of this invention will occur to those skilled in the art. All such modifications coming within the scope of the appended claims are intended to be included therein.

What is claimed is:

1. A method for preventing the onset of an autoimmune or inflammatory disease in a patient at risk for developing an autoimmune or inflammatory disease which method comprises:

(a) identifying a patient at risk for developing an autoimmune or inflammatory disease;

(b) administering to said patient a pharmaceutical composition comprising a pharmaceutically acceptable carrier and an effective autoimmune or inflammatory disease-preventing amount of a compound of formula I:

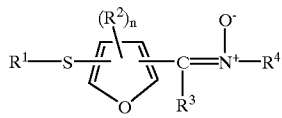
I wherein
$R^1$ is selected from the group consisting of alkyl, substituted alkyl, alkenyl, substituted alkenyl, alkynyl, aralkyl, aryl, cyloalkyl, cycloalkylalkyl and cycloalkenyl;
each $R^2$ is independently selected from the group consisting of alkyl, substituted alkyl, alkenyl, substituted alkenyl, alkynyl, aralkyl, aryl, alkoxy, substituted alkoxy, cycloalkyl and halo;
$R^3$ is selected from the group consisting of hydrogen, alkyl, substituted alkyl, alkenyl, substituted alkenyl, alkynyl, aralkyl, aryl, cycloalkyl and cycloalkylalkyl;
$R^4$ is selected from the group consisting of alkyl, substituted alkyl, alkenyl, substituted alkenyl, alkynyl, aralkyl, aryl, cycloalkyl, cycloalkylalkyl and cycloalkenyl; and
n is an integer ranging from 0 to 2; and optical isomers and racemates thereof, and pharmaceutically acceptable salts thereof.

2. The method according to claim 1 wherein the autoimmune disease is systemic lupus or multiple sclerosis.

3. The method according to claim 1 wherein the inflammatory disease is rheumatoid arthritis, septic shock, erythema nodosum leprosy, septicemia, uveitis, adult respiratory distress syndrome or inflammatory bowel disease.

4. The method of claim 1 wherein n is 0.

5. The method of claim 4 wherein $R^3$ is hydrogen.

6. The method of claim 5 wherein $R^1$ is a substituted phenyl group having the formula:

wherein
each $R^5$ is independently selected from the group consisting of alkyl, substituted alkyl, cycloalkyl, aralkyl, aryl, alkoxy, substituted alkoxy, aryloxy, arakyloxy, cycloalkoxy, acyl, acylamino, aminocarbonyl, alkoxycarbonyl, carboxyl, cyano, halo, hydroxy, nitro, sulfonate, thioalkoxy, and —$NR^6R^7$, where $R^6$ and $R^7$ are each independently selected from hydrogen, alkyl, substituted alkyl or aryl; or two adjacent $R^5$ groups can be joined together to form an alkylene or alkylenedioxy group; and
m is an integer from 1 to 5.

7. The method of claim 6 wherein $R^5$ is selected from the group consisting of alkyl, alkoxy, substituted alkoxy, acylamino, thioalkoxy.

8. The method of claim 7 wherein $R^5$ is a methyl, methoxy, trifluoromethoxy, acetamido or thiomethoxy group and m is 1 or 2.

9. The method of claim 5 wherein $R^1$ is selected from the group consisting of 2-methoxyphenyl, 4-methoxyphenyl, 4-trifluoromethoxyphenyl, 3,5-dimethylphenyl, 4-acetamidophenyl and 4-thiomethoxyphenyl.

10. The method of claim 4 wherein $R^4$ is selected from the group consisting of alkyl, substituted alkyl, aralkyl, cycloalkyl and cycloalkylalkyl.

11. The method of claim 10 wherein $R^4$ is alkyl or cycloalkyl.

12. The method of claim 11 wherein $R^4$ is selected from the group consisting of n-propyl, isopropyl, tert-butyl, cyclopentyl, cyclohexyl and 2,4,4-trimethypent-2-yl.

13. The method of claim 1 wherein the compound of formula I is selected from a compound of formula II:

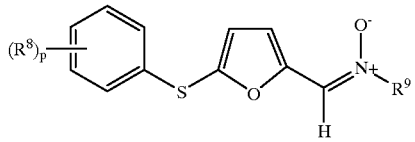
II wherein
each $R^8$ is independently selected from the group consisting of alkyl, alkoxy, acylamino, trifluoromethoxy and thioalkoxy;
$R^9$ is selected from the group consisting of alkyl and cycloalkyl; and
p is an integer ranging from 1 to 3;
and optical isomers and racemates thereof, and pharmaceutically acceptable salts thereof.

14. The method of claim 13 wherein $R^8$ is a methyl, methoxy, trifluoromethoxy, acetamido or thiomethoxy group and p is 1 or 2.

15. The method of claim 13 wherein $R^9$ is n-propyl, isopropyl, tert-butyl, cyclopentyl, cyclohexyl or 2,4,4-trimethylpent-2-yl.

16. The method of claim 1 wherein the compound of formula I is selected from:
α-[2-(4-methoxyphenylthio)-5-furyl]-N-tert-butylnitrone,
α-[2-(2-methoxyphenylthio)-5-furyl]-N-tert-butylnitrone,
α-[2-(4-methoxyphenylthio)-5-furyl]-N-cyclohexylnitrone,
α-[2-(4-trifluoromethoxypbenylthio)-5-furyl]-N-tert-butylnitrone,
α-[2-(3,5-dimethylphenylthio)-5-furyl]-N-tert-butylnitrone,
α-[2-(4-acetamidophenylthio)-5-furyl]-N-tert-butylnitrone,
α-[2-(4-ethylphenylthio)-5-furyl]-N-tert-butylnitrone,
α-[2-(4-thiomethoxyphenylthio)-5-furyl]-N-tert-butylnitrone,
α-[2-(4-methoxyphenylthio)-5-furyl]-N-isopropylnitrone,
α-[2-(4-trifluoromethoxypbenylthio)-5-furyl]-N-cyclohexylnitrone,
α-[2-(4-methoxyphenylthio)-5-furyl]-N-n-butylnitrone,
α-[2-(4-methoxyphenylthio)-5-furyl]-N-n-propylnitrone,
α-[2-(4-trifluoromethoxyphenylthio)-5-furyl]-N-isopropylnitrone,
α-[2-(4-trifluoromethoxyphenylthio)-5-furyl]-N-n-propylnitrone,
α-[2-(4-methoxyphenylthio)-5-furyl]-N-2,4,4-trimethylpent-2-ylnitrone,
α-[2-(4-trifluoromethoxyphenylthio)-5-furyl]-N-2,4,4-trimethylpent-2-ylnitrone,
α-[2-(4-methoxyphenylthio)-5-furyl]-N-cyclopentylnitrone, or
α-[2-(4-trifluoromethoxyphenylthio)-5-furyl]-N-cyclopentylnitrone.

* * * * *